(12) United States Patent
Lipoma et al.

(10) Patent No.: US 7,494,498 B2
(45) Date of Patent: *Feb. 24, 2009

(54) LANCING DEVICE WITH FLOATING LANCET

(75) Inventors: Michael V. Lipoma, Villa Rica, GA (US); Avi M. Robbins, Longwood, FL (US); Carl E. Griffin, Marietta, GA (US); David R. Buenger, Roswell, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 703 days.

This patent is subject to a terminal disclaimer.

(21) Appl. No.: 10/807,901

(22) Filed: Mar. 24, 2004

(65) Prior Publication Data
US 2004/0260326 A1    Dec. 23, 2004

Related U.S. Application Data

(60) Provisional application No. 60/456,927, filed on Mar. 24, 2003.

(51) Int. Cl.
*A61B 17/34* (2006.01)

(52) U.S. Cl. .................................................. 606/182

(58) Field of Classification Search .......... 606/181–183, 606/185; 600/583; 604/156, 157
See application file for complete search history.

(56) References Cited

U.S. PATENT DOCUMENTS

| 4,449,529 | A | 5/1984 | Burns et al. |
|---|---|---|---|
| 4,503,856 | A | 3/1985 | Cornell et al. |
| 4,527,561 | A | 7/1985 | Burns |
| 4,535,769 | A | 8/1985 | Burns |
| 4,553,541 | A | 11/1985 | Burns |
| 4,616,649 | A | 10/1986 | Burns |
| 4,817,603 | A | 4/1989 | Turner et al. |
| RE32,922 | E * | 5/1989 | Levin et al. ............ 606/182 |
| 4,895,147 | A | 1/1990 | Bodicky et al. |
| 4,924,879 | A | 5/1990 | O'Brien |
| 4,990,154 | A | 2/1991 | Brown et al. |
| 5,074,872 | A | 12/1991 | Brown et al. |
| 5,282,822 | A | 2/1994 | Macors et al. |
| 5,318,854 | A | 6/1994 | Lange et al. |
| 5,356,420 | A | 10/1994 | Czernecki et al. |

(Continued)

OTHER PUBLICATIONS

Sutor et al., "Bleeding from Standardized Skin Punctures: Automated Technic for Recording Time, Intensity, and Pattern of Bleeding," Jou.C.P., vol. 55, May 1971, pp. 541-549.

(Continued)

*Primary Examiner*—Todd E Manahan
*Assistant Examiner*—Elizabeth Houston
(74) *Attorney, Agent, or Firm*—Gardner Groff Greenwald & Villanueva, PC

(57) ABSTRACT

A lancing device including a drive mechanism with a drive spring and a lancet carrier engaged and driven by the drive spring, and further including a lancet with a sharp lancing tip, wherein the lancet floats relative to the carrier and is decoupled from the drive mechanism during at least a portion of a lancing stroke. In one example embodiment the lancet is held in a sled that floats in the carrier, and in another example embodiment the lancet by itself floats in the carrier.

20 Claims, 13 Drawing Sheets

U.S. PATENT DOCUMENTS

| | | | |
|---|---|---|---|
| 5,368,047 A | 11/1994 | Suzuki et al. | |
| 5,569,287 A | 10/1996 | Tezuka et al. | |
| 5,611,809 A | 3/1997 | Marshall et al. | |
| 5,613,978 A | 3/1997 | Harding | |
| D379,516 S | 5/1997 | Rutter | |
| 5,628,764 A | 5/1997 | Schraga | |
| 5,730,753 A | 3/1998 | Morita | |
| 5,741,288 A | 4/1998 | Rife | |
| 5,879,311 A | 3/1999 | Duchon et al. | |
| 5,885,211 A | 3/1999 | Eppstein et al. | |
| 5,908,434 A | 6/1999 | Schraga | |
| 5,916,230 A | 6/1999 | Brenneman et al. | |
| 5,938,679 A | 8/1999 | Freeman | |
| 5,964,718 A * | 10/1999 | Duchon et al. | 600/583 |
| 5,984,940 A | 11/1999 | Davis et al. | |
| 6,022,366 A | 2/2000 | Schraga et al. | |
| 6,045,567 A | 4/2000 | Taylor et al. | |
| 6,056,701 A | 5/2000 | Duchon et al. | |
| 6,066,103 A | 5/2000 | Duchon et al. | |
| 6,086,545 A | 7/2000 | Roe et al. | |
| 6,139,562 A | 10/2000 | Mauze et al. | |
| 6,156,050 A | 12/2000 | Davis et al. | |
| 6,156,051 A | 12/2000 | Schraga | |
| 6,171,325 B1 | 1/2001 | Mauze et al. | |
| 6,176,865 B1 | 1/2001 | Mauze et al. | |
| 6,197,040 B1 * | 3/2001 | LeVaughn et al. | 606/182 |
| 6,231,531 B1 | 5/2001 | Lum et al. | |
| 6,248,120 B1 | 6/2001 | Wyszogrodzki | |
| 6,283,982 B1 | 9/2001 | Levaughn et al. | |
| 6,306,152 B1 | 10/2001 | Verdonk et al. | |
| 6,322,575 B1 | 11/2001 | Schraga | |
| 6,451,040 B1 | 9/2002 | Purcell | |
| 6,464,649 B1 | 10/2002 | Duchon et al. | |
| 6,514,270 B1 * | 2/2003 | Schraga | 606/182 |
| 6,530,937 B1 | 3/2003 | Schraga | |
| 6,558,402 B1 | 5/2003 | Chelak et al. | |
| 6,613,064 B2 | 9/2003 | Rutynowski et al. | |
| 6,645,219 B2 * | 11/2003 | Roe | 606/182 |
| 6,660,018 B2 | 12/2003 | Lum et al. | |
| 6,730,046 B1 * | 5/2004 | Hamamoto et al. | 600/583 |
| 6,929,650 B2 * | 8/2005 | Fukuzawa et al. | 606/182 |
| 6,949,111 B2 | 9/2005 | Schraga | |
| 6,969,359 B2 | 11/2005 | Duchon et al. | |
| 7,288,102 B2 | 10/2007 | Griffin et al. | |
| 2001/0027327 A1 | 10/2001 | Schraga | |
| 2002/0029059 A1 | 3/2002 | Purcell | |
| 2003/0018282 A1 | 1/2003 | Effenhauser et al. | |
| 2003/0088261 A1 | 5/2003 | Schraga | |
| 2003/0225430 A1 | 12/2003 | Schraga | |
| 2004/0059366 A1 * | 3/2004 | Sato et al. | 606/182 |
| 2004/0098010 A1 | 5/2004 | Davison et al. | |
| 2004/0254599 A1 | 12/2004 | Lipoma et al. | |
| 2004/0260326 A1 | 12/2004 | Lipoma et al. | |
| 2005/0038464 A1 * | 2/2005 | Shraga | 606/182 |

OTHER PUBLICATIONS

Bayer, "Ames Glucolet" lancing device; 2 pgs.
Bayer, "Microlet" lancing device; 2 pgs.
Bayer, "Vaculance" lancing device, 1 pg.
Bechton-Dickinson, "Autolance" lancing device; 2 pgs.
Lifescan/Johnson & Johnson, Penlet Plus, lancing device; 2 pgs.
Lifescan, "Penlet II" lancing device; 2 pgs.
Palco, "Auto-Lancet" lancing device: 2 pgs.
Roche, "Autoclix" lancing device: 2 pgs.
Roche. Soft Touch II lancing device; 1 pg.

* cited by examiner

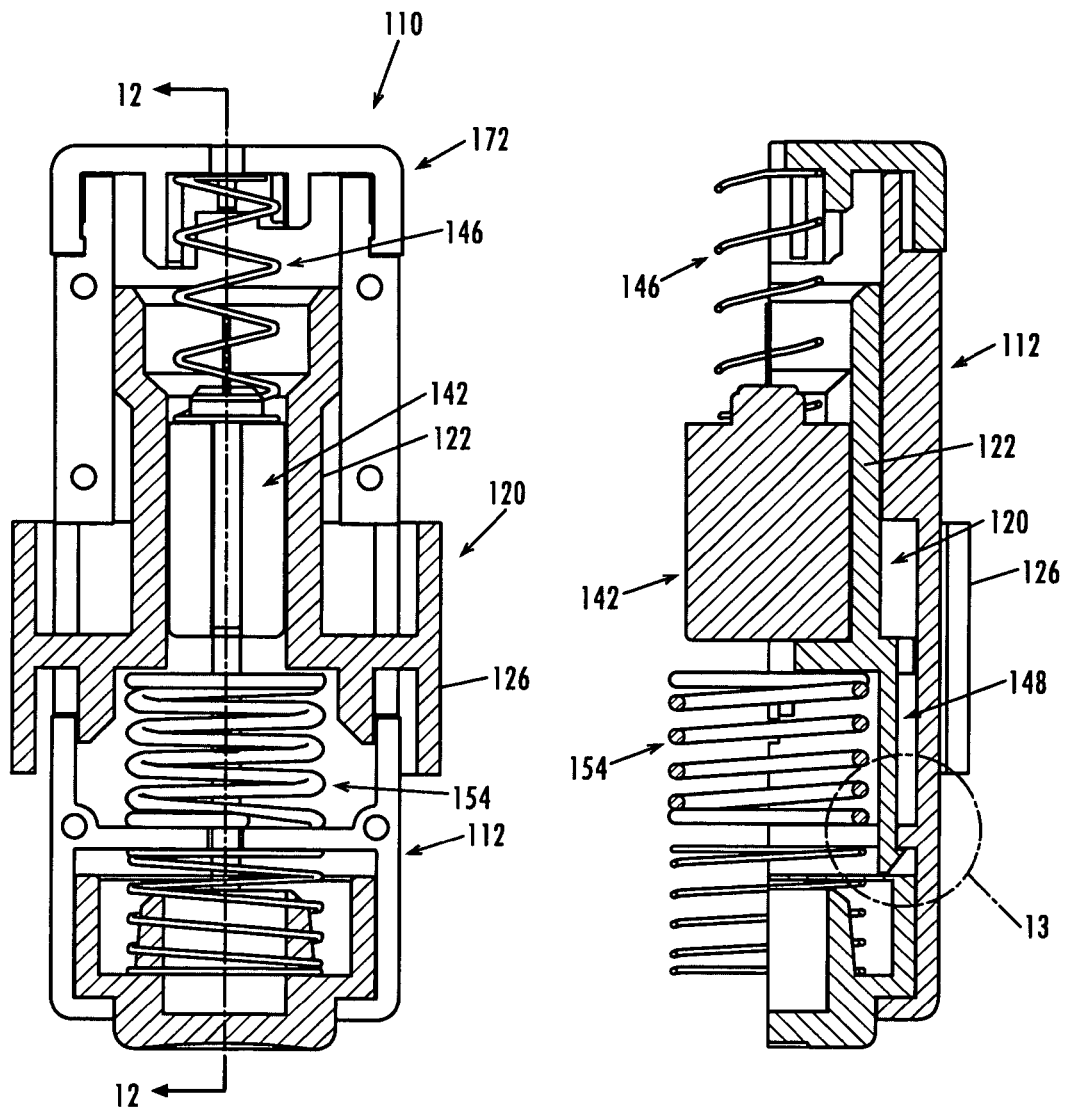
*Fig. 11*
*Fig. 12*
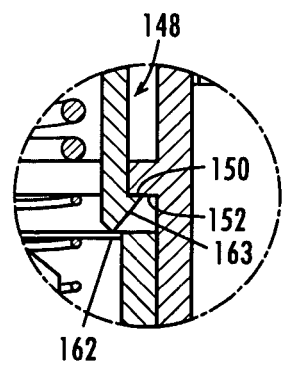
*Fig. 13*

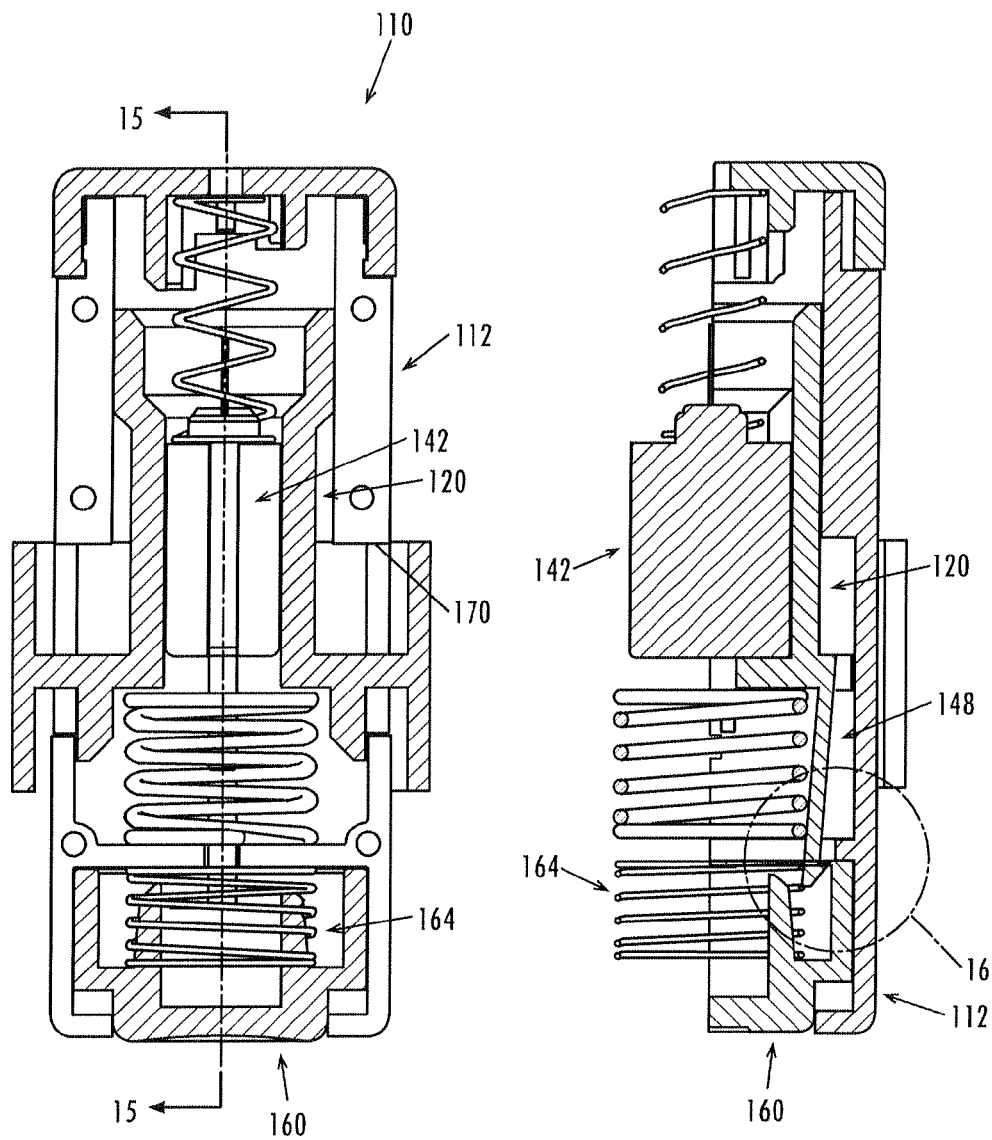
*Fig. 14*    *Fig. 15*
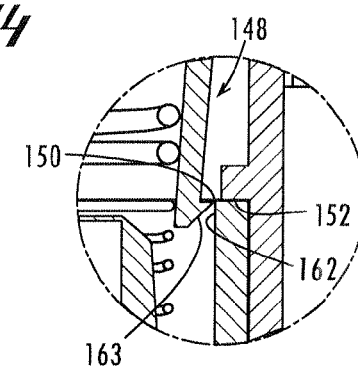
*Fig. 16*

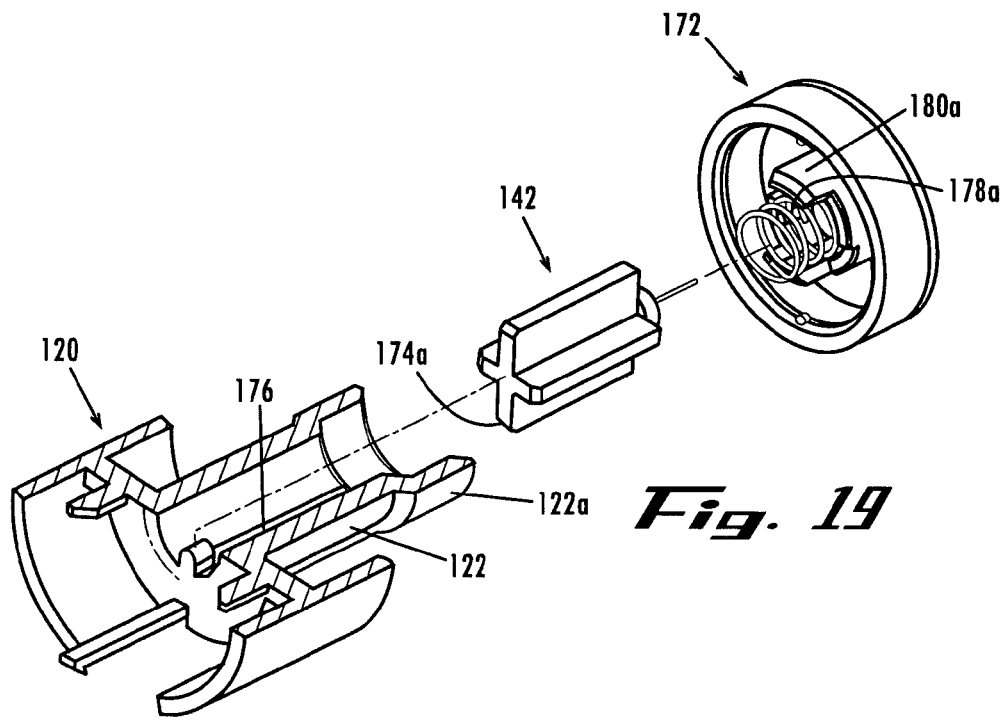
Fig. 19
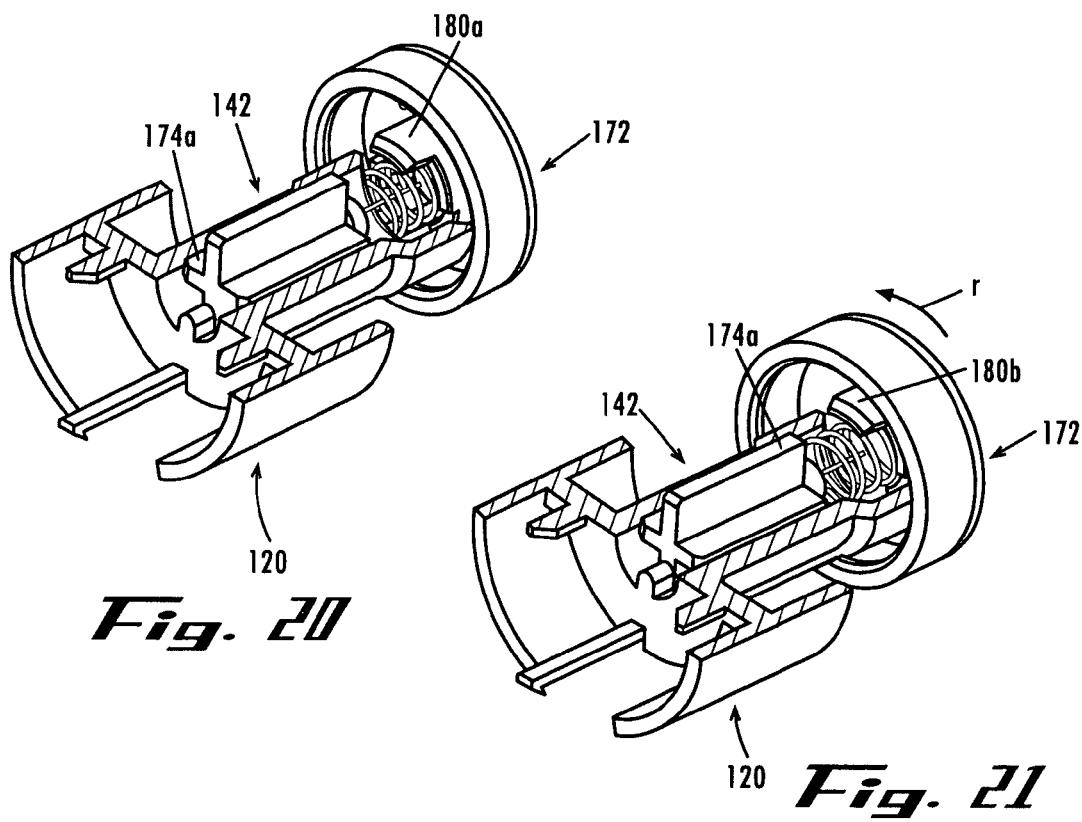
Fig. 20
Fig. 21

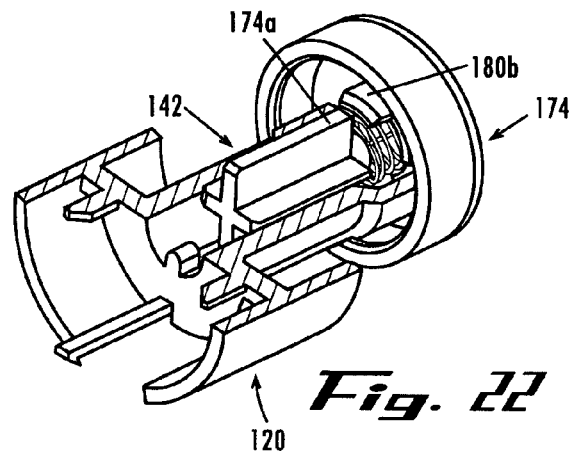
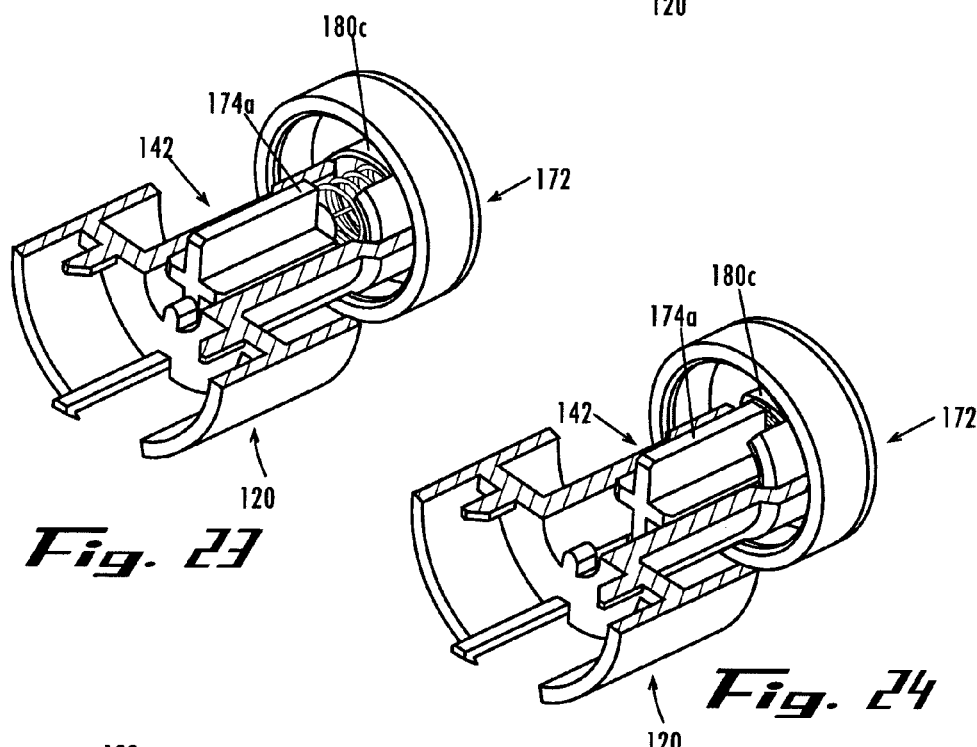
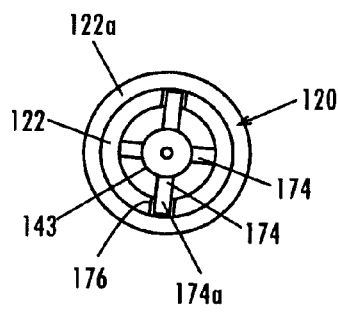
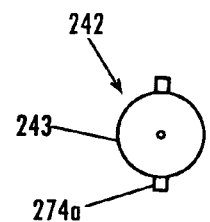

LANCING DEVICE WITH FLOATING LANCET

CROSS-REFERENCE TO RELATED APPLICATION

This application claims the priority benefit of U.S. Provisional Application Ser. No. 60/456,927, filed Mar. 24, 2003, which is hereby incorporated by reference herein.

FIELD OF THE INVENTION

The present invention relates generally to the field of medical sampling devices, and more particularly to a lancing device having a precision-guided, high-velocity, low-mass lancet, which is inertially propelled and floats within a sliding lancet carrier.

BACKGROUND OF THE INVENTION

Various lancing devices are known for penetrating the skin of a human or animal subject at a lancing site for obtaining a sample of blood or other body fluids. In general, a typical lancing device includes a housing containing a lancet connected to a spring-driven drive mechanism, a cocking mechanism for arming or energizing the drive-spring, and a trigger mechanism for releasing the drive mechanism to complete the lancing operation.

In order to encourage compliance with a prescribed sampling regimen, for example as in blood glucose sampling by diabetics, it is desirable to minimize the pain and discomfort resulting from the lancing procedure. To date, efforts to minimize pain from lancing have largely focused on controlling the depth of penetration into the subject's skin at the lancing site. For example, many lancing devices include a depth-control mechanism for varying the depth of penetration, either by adjusting the distance of travel of the lancet tip, or by adjusting the position of an endcap through which the lancet protrudes during the lancing operation.

Advances in lancing device technology have, to some extent, reduced the pain associated with the lancing process. However, further improvement in reducing pain and discomfort associated with the lancing process is a continuing need. It is to an improved lancing device meeting this and other needs that the present invention is primarily directed.

SUMMARY OF THE INVENTION

The present invention provides improved lancing devices having a low-mass lancet carried in a carrier. The lancet and carrier arrangement provides precision guidance of the lancet to minimize rocking and lateral movement of the lancet as it punctures the skin at the lancing site, minimizing tearing of tissue and resultant pain. The lancet and carrier are inertially propelled through a high-velocity lancing stroke, with the lancet floating within a bore in the carrier and not in direct engagement with the drive mechanism. This results in a lower mass behind the lancet and a higher lancet velocity during puncturing. The combination of low mass and high lancing stroke velocity has been found to further minimize the pain sensed by a human or animal subject.

Generally described, the present invention includes a multi-use or disposable lancing device comprising a drive mechanism and a lancet. The drive mechanism includes a drive spring and a carrier that is driven by the drive spring through a lancing stroke. The lancet is slidingly engaged by the carrier and, during at least a portion of a lancing stroke, floats relative to the carrier and is decoupled from the drive mechanism. In this way, the carrier engages and drives the lancet through a first portion of the lancing stroke, and then the lancet is inertially propelled through a second portion of the lancing stroke after the carrier is stopped.

In a first example embodiment, the lancet is received in or is a part of a sled, which in turn is slidably received in the carrier. In a second example embodiment, the lancet is slidably received directly in the carrier. In either embodiment, a carrier stop member is provided that limits the travel of the carrier, but not the lancet/sled, before the lancet/sled reaches an extended position. A lancet stop member limits the travel of the lancet/sled in the extended position, the lancet stop preferably being a separate structure from the carrier stop.

In another aspect of the invention, the carrier comprises a carriage that is slidably received in the housing chamber and that has a bore that slidably receives the lancet. The carrier further comprises one or more wings extending outwardly of the housing. In this way, the lancing device can be armed by retracting the wings to a cocked position with the carrier in a retracted position. Preferably, one or more struts extend between the carriage and the wings, and project through one or more slots in the housing. In this way, after the lancing device is fired but before the lancet reaches an extended position, the carrier is stopped by the carrier struts engaging one or more stop surfaces defined by the housing slots.

In yet another aspect of the invention, the lancing device includes a cocking mechanism comprising at least one cocking arm and at least one engagement surface. The cocking arm extends from the sled, the lancet, the carrier, or another component of the drive mechanism. The engagement surface is positioned on the housing or elsewhere for retaining the cocking arm in a cocked position with the carrier in a retracted position. Also, a trigger mechanism includes a release button with a catch release member that, when the release button is moved, engages the cocking arm and releases the carrier to move to the extended position for puncturing skin at the lancing site.

And in still another aspect of the invention, the lancing device has a penetration depth adjustment mechanism comprising an endcap that rotates relative to the lancing device housing. The lancet includes at least one engagement surface, and the endcap has a plurality of stop surfaces that can be selectively aligned with and engaged by the lancet engagement surface to limit forward lancet movement at different depths. In addition, the carriage preferably has a flared proximal section with a flared bore that receives the endcap stop surfaces not aligned with and engaged by the lancet body engagement surface.

In another aspect of the invention, the present invention includes methods of lancing the skin of a subject to obtain a sample of body fluid. The methods preferably include driving a lancet or a lancet-holding sled through a first portion of a lancing stroke by engagement with a carrier and a drive mechanism; stopping the motion of the carrier; and allowing the lancet or a lancet-holding sled to continue through a second portion of the lancing stroke after the carrier is stopped. Preferably, the carrier is stopped by impacting the carrier, but not the lancet, against a carrier stop surface before the lancet reaches an extended position.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING FIGURES

FIG. 3 is a longitudinal cross-section view of the lancing device of FIG. 1, in an armed state.

FIG. 12 is a cross-section view of the lancing device taken at line G-G of FIG. 11.

FIG. 13 is a cross-section detail view, Detail "H" of FIG. 12, showing the cocking arm catch being retained in place.

FIG. 14 is a longitudinal cross-section view of the lancing device of FIG. 5, with the lancet and carrier in an activated or firing position.

FIG. 15 is a cross-section view of the lancing device taken at line J-J of FIG. 14.

FIG. 16 is a cross-section detail view, Detail "K" of FIG. 15, showing the cocking arm catch being released for firing.

FIG. 17 is a longitudinal cross-section view of the lancing device of FIG. 5, with the carrier in a stopped position.

FIG. 19 is an exploded perspective view of the carrier (in cross section), lancet, and endcap of the lancing device of FIG. 5.

FIG. 20 is a perspective view of the carrier (in cross section), lancet, and endcap of FIG. 19, with the endcap in a safety position.

FIG. 21 is a perspective view of the carrier (in cross section), lancet, and endcap of FIG. 19, with the endcap in a shallow puncturing depth position.

FIG. 22 is a perspective view of the carrier (in cross section), lancet, and endcap of FIG. 21, with the lancet fired and in the puncturing position.

FIG. 23 is a perspective view of the carrier (in cross section), lancet, and endcap of FIG. 19, with the endcap in a deep puncturing depth position.

FIG. 24 is a perspective view of the carrier (in cross section), lancet, and endcap of FIG. 23, with the lancet fired and in the puncturing position.

FIG. 25 is a front view of the carrier and lancet of FIG. 19.

FIG. 26 is a front view of an alternative lancet for use with the carrier and endcap of FIG. 19.

DETAILED DESCRIPTION OF EXAMPLE EMBODIMENTS

Figure 1:
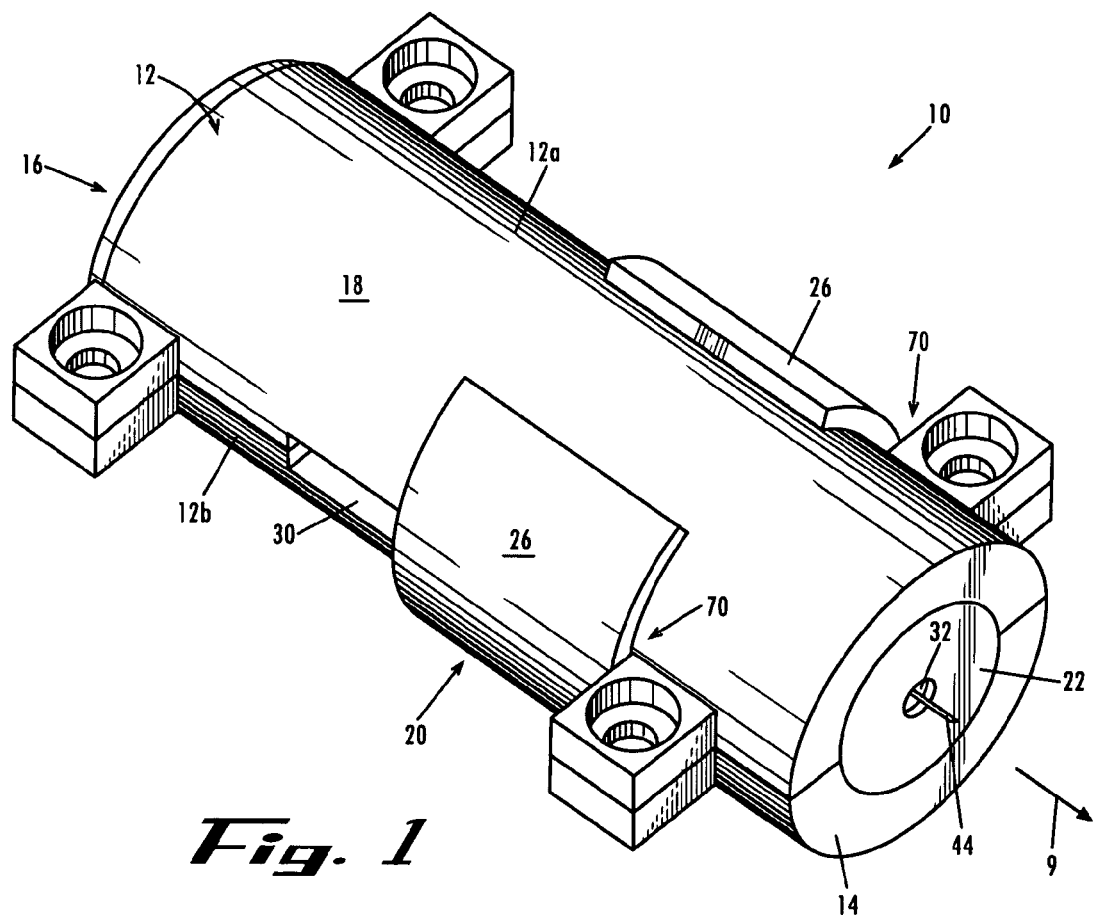
FIG. 1 is a perspective view of a lancing device according to a first example embodiment of the present invention.

Referring now to the drawing figures, wherein like reference numerals represent like parts throughout, preferred forms of the present invention will now be described. It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. In addition, as used in the specification including the appended claims, the singular forms "a," "an," and "the" include the plural, plural forms include the singular, and reference to a particular numerical value includes at least that particular value, unless the context clearly dictates otherwise. Furthermore, any methods described herein are not intended to be limited to the sequence of steps described but can be carried out in other sequences, unless expressly stated otherwise herein.

Figure 2:
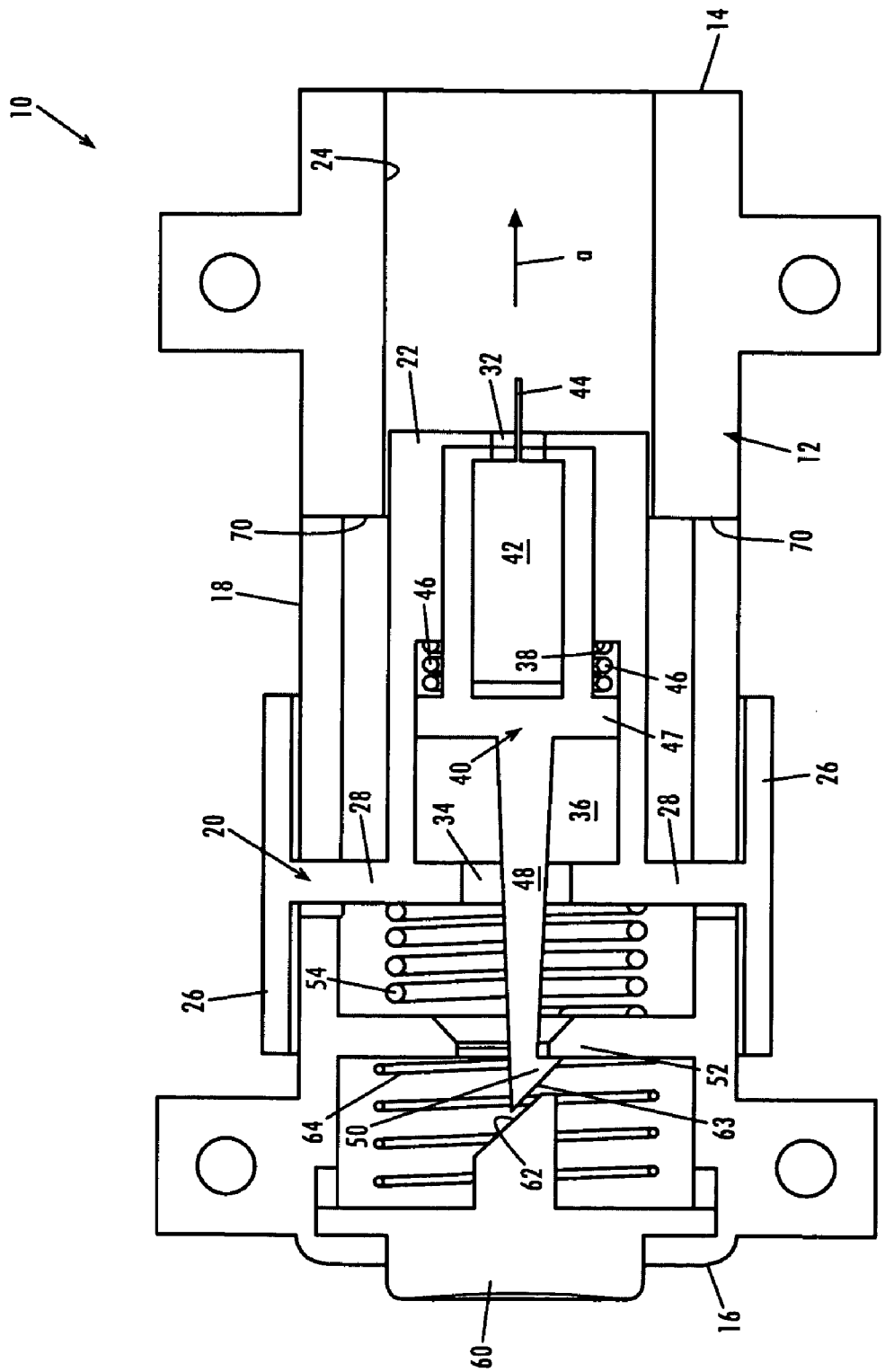
FIG. 2 is a longitudinal cross-section view of the lancing device of FIG. 1, with the lancet carrier in a retracted position for cocking the device.
Figure 1:
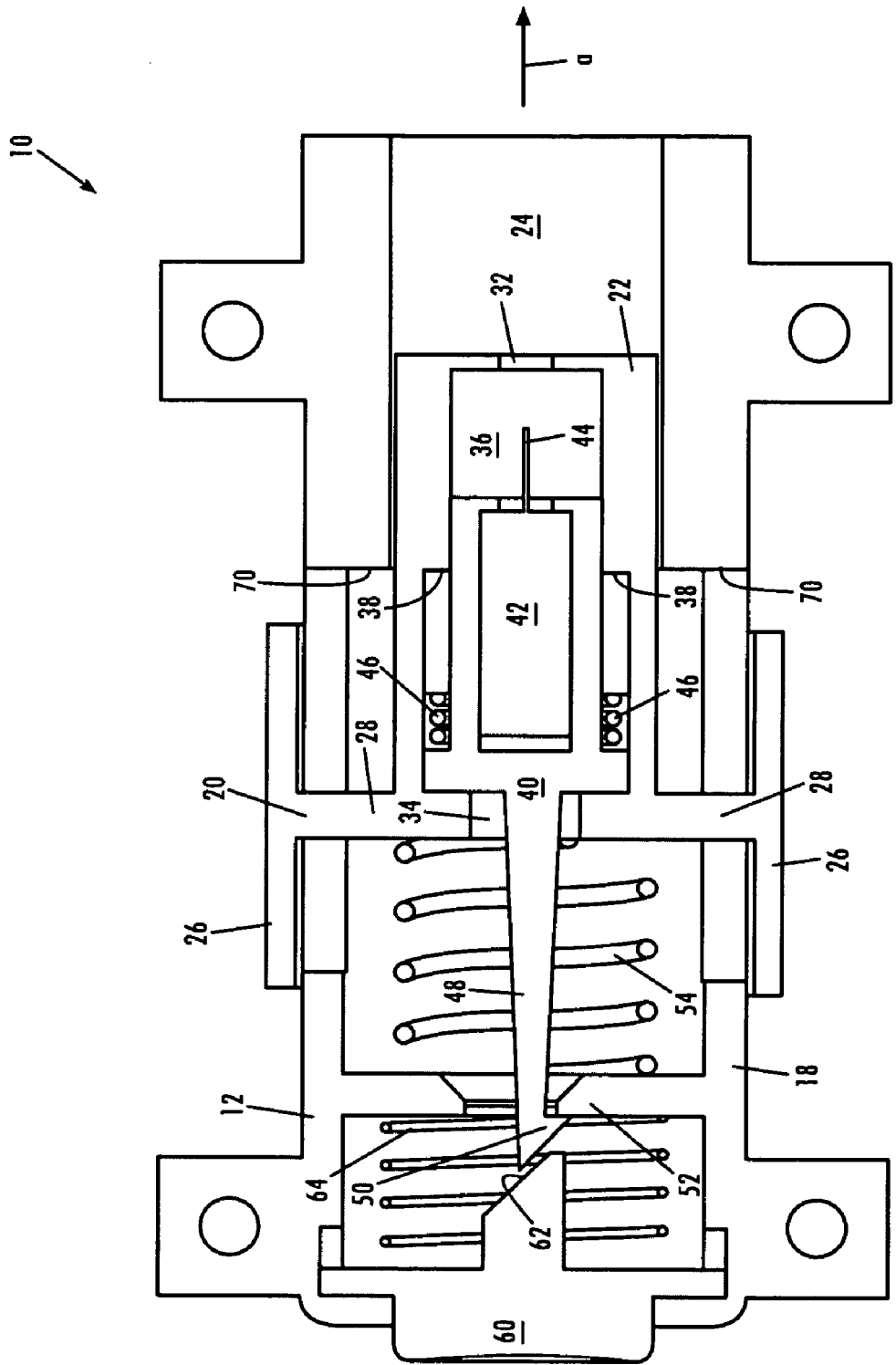

FIGS. 1-4 show a lancing device 10 according to a first example embodiment of the invention. Referring to FIGS. 1 and 2, the device 10 includes a housing 12, preferably formed of two inter-engaging half-shells 12a, 12b. Generally, the housing 12 has a proximal end 14, a distal end 16, and one or more sidewalls 18. In the depicted embodiment, the housing 12 is generally cylindrical and is formed of plastic and/or other substantially rigid material(s), as for example by injection molding. It will be understood that other housing configurations and materials may be suitably used. In addition, a penetrable foil covering or removable cap (unshown) preferably initially covers the opening at the proximal end 14 of the housing 12 to maintain sterility prior to use of the device 10.

A drive mechanism includes a drive member such as a carrier 20 that is slidably mounted to the housing 12. The carrier 20 preferably includes a carriage 22 mounted within a channel 24 extending axially through the housing 12, and one or more sleeves or wings 26 extending outwardly of the housing 12 and connected to the carriage by a strut 28 projecting through a slot 30 in the sidewall 18 of the housing. The carriage 22 is preferably engaged within the channel 24 with a close sliding fit to minimize rocking and lateral motion, and to constrain the carriage to translation along an axial path parallel to direction arrow "a." The struts 28 preferably slide within the slot 30 with a close sliding fit, further defining the path of translation of the carrier 20 and preventing twisting of the carrier within the housing 12. The sleeves or wings 26 provide a gripping surface for the user to grasp to pull back the carrier 20 for cocking the lancing device. As such, the wings 26 may be provided by tabs, collars, finger rests, and other grasping members. In the depicted embodiment, for example, the wings 26 generally conform to the shape of the housing 12 and are in the form of sleeves that extend a majority of the way around the housing.

In addition, a proximal hole or opening 32 is formed in the proximal face of the carriage 22 of the carrier 20 for allowing passage of a lancet tip during lancing, as described below. A distal hole or opening 34 is formed in the distal face of the carriage 22 of the carrier 20 for allowing passage through it of a cocking arm portion of the lancet sled, as described below. And a stepped bore 36 (including a track, channel, etc.) preferably extends axially through the carriage 22 of the carrier 20, forming a distally-facing shoulder 38.

A lancet sled 40 is slidably mounted within the bore 36 of the carriage 22, and includes a lancet 42 having a sharp lancing tip 44. The bore 36 is preferably cylindrical, but it may have a square of other cross-sectional shape, if desired, and is axially longer than a body of the lancet 42. The lancet 42 may be integrally formed with the lancet sled 40, for example, in a disposable lancing device embodiment. Or it may be a separate component secured to the sled, as by a friction fit within a receptacle of the sled as shown, for example, in a multi-use lancing device embodiment. The sled 40 and lancet 42 preferably have a low mass relative to known lancet and drive mechanisms. A return spring 46 is preferably engaged between a flange or projection 47 extending from the lancet sled, and the shoulder 38 of the carrier 20.

A cocking mechanism preferably comprises at least one cocking arm 48 that extends distally from the lancet sled 40 and includes a catch such as a barb 50 for engaging an engagement surface such as a flange or shoulder 52 of the housing 12 to secure the sled and carrier arrangement in a cocked position, as shown in FIG. 2. Alternatively, the cocking arm 48 may extend from the carrier 20, from the lancet 42 (e.g., in embodiments with the lancet and sled integrally formed as one piece), or from another component of the device 10. And the drive mechanism includes a drive spring 54 that is preferably engaged between the carrier 20 and the housing 12, for driving the lancet sled 40 and carrier 20 through a lancing stroke from the cocked position (see FIG. 2) to the extended position (see FIG. 4). It will be understood that other conventional cocking mechanisms may be suitably employed.

A trigger mechanism includes a trigger or release button 60 that is preferably mounted at the distal end 16 of the housing 12. The release button 60 includes a catch release member such as an inclined cam face 62 for engagement against a cooperating inclined face 63 or other catch release member of the cocking arm 48. A spring 64 is preferably provided to bias the release button 60 distally from the housing 12. When the release button 60 is depressed, the inclined cam face 62 engages the cooperating inclined face 63 to release the barb 50 from the shoulder 52, thereby firing the device 10 and initiating a lancing operation. It will be understood that other conventional trigger mechanisms may be suitably employed.

Figure 4:
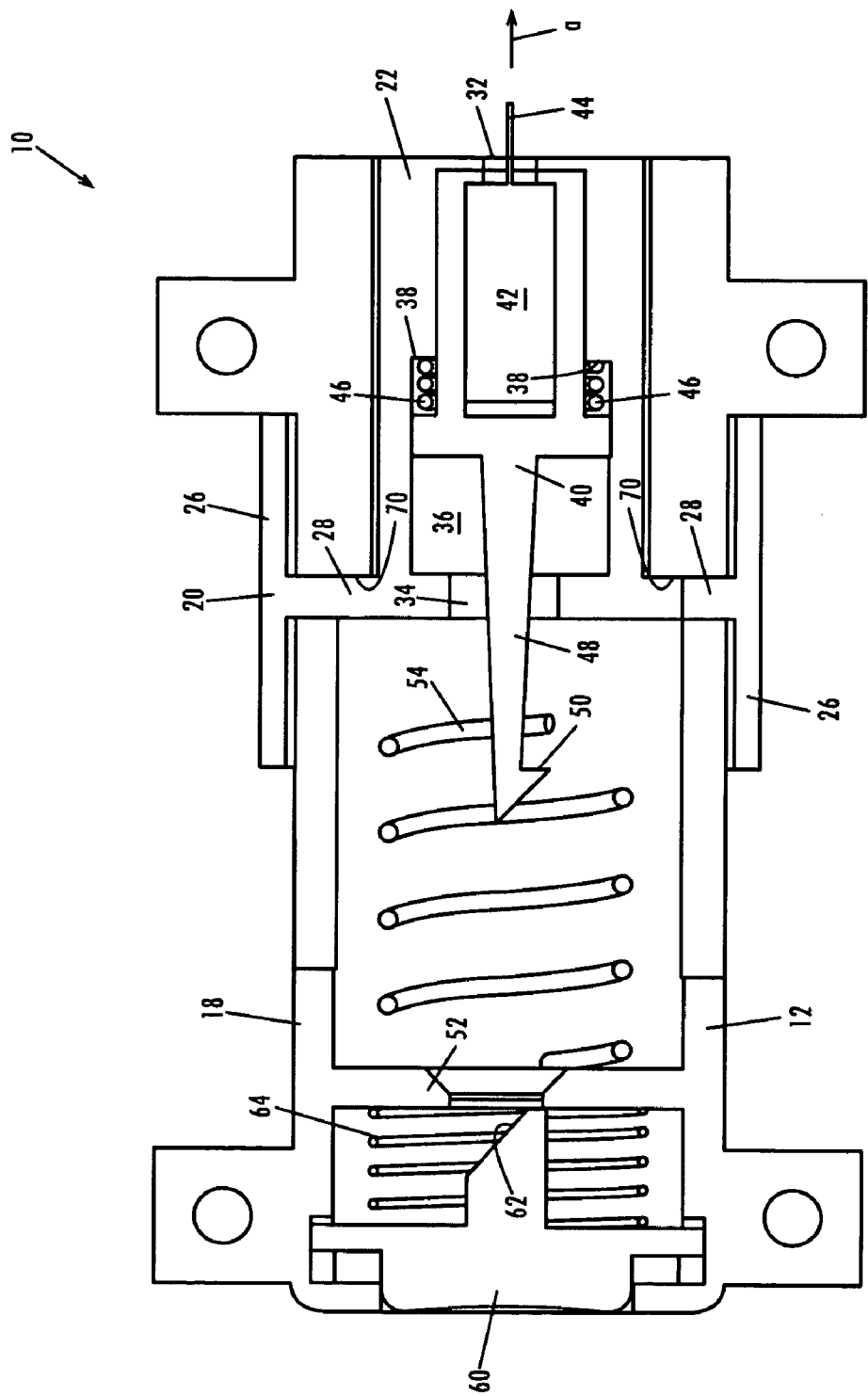
FIG. 4 is a longitudinal cross-section view of the lancing device of FIG. 1, with the lancet in an extended position of the lancing stroke for puncturing the skin.
Figure 5:
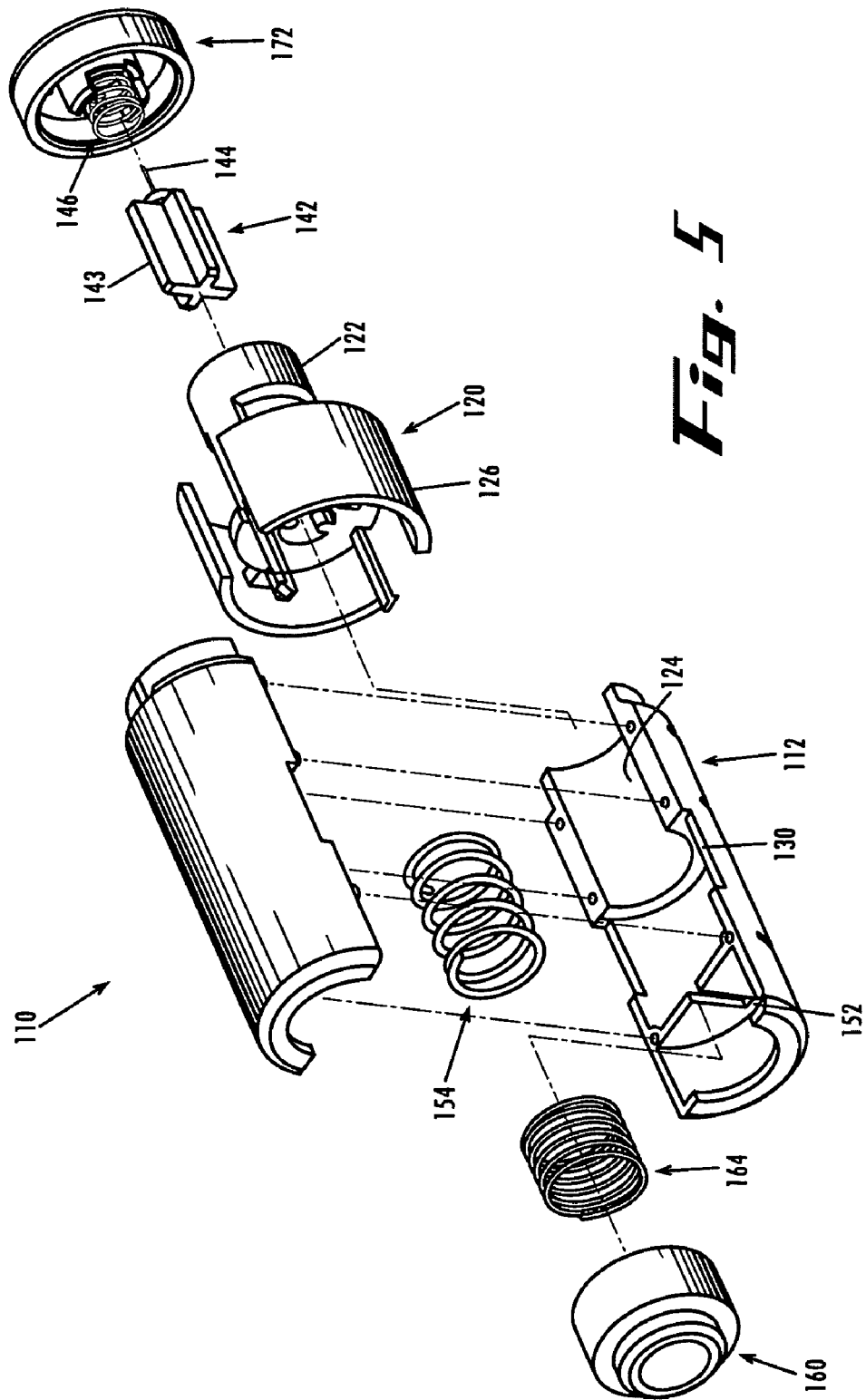
FIG. 5 is an exploded perspective view of a lancing device according to a second example embodiment of the present invention.

FIGS. 2-4 depict a sequence of operation of the lancing device 10 and a first example method of lancing according to the present invention. The lancing device 10 is preferably delivered to the user in an uncocked state, with the drive spring 54 substantially or partially relaxed. The user cocks the device 10 by gripping the housing 12 and the wings 26, and pulling the wings (and thereby the carriage 22 and sled 40) distally relative to the housing, into the cocked position shown in FIG. 2, with the drive spring 54 substantially fully compressed. Interaction between the shoulder 38 of the carriage 22 and the flange 47 of the sled 40 withdraws the sled distally along with the carrier during cocking. Engagement of the catch barb 50 with the engagement shoulder 52 retains the carrier 20 in a cocked position after the wings 26 are released, allowing the carrier to move forward (proximally) within the channel 24 under the biasing influence of the drive spring 54, as shown in FIG. 3. The user then places the proximal face 14 of the housing 12 against the skin at the sampling site of a human or animal subject. The device 10 is fired to complete the lancing operation by pressing the release button 60, the inclined face 62 of which contacts the cooperating inclined face 63 of the cocking arm 48 and disengages the catch barb 50 from the engagement shoulder 52. Then the drive spring 54 propels the sled carrier 20 and the lancet sled 40 forward to initiate the lancing stroke.

When the lancing stroke begins, the sled 40 is retained in a retracted position, toward the distal end of the bore 36 in the carriage 22. The sled 40 is retracted in the back of the bore 36 as a result of the engagement of the barb 50 and the shoulder 52 holding the carrier back, combined with the forward bias of the drive spring 54 against the carrier 20 (see FIG. 3). After operating the trigger to fire the device 10, the carrier 20 is released and now moves forward under the influence of the drive spring 54, carrying the lancet sled 40 along with it. The carrier 20 and lancet sled 40 move forward together until there is an impact with a carrier stop such as a proximal endwall 70 of the slot 30 of the housing 12. For example, the stopping may be caused by the carrier struts 28 impacting the housing slot proximal endwalls 70, the carrier wings 126 impacting a protruding structure on the exterior of the housing 12, or by other means. Inertia propels the lancet sled 40 forward after the carrier 20 stops, with the sled 40 and lancet 42 no longer being coupled to the carrier 20 or the spring 44 of the drive mechanism.

The sled 40 slides forward through the bore 36 to the extended position, shown in FIGS. 1 and 4, wherein the sharp lancet tip 44 passes through the hole 32 and projects a distance beyond the proximal face of the housing 12 to puncture the subject's skin at the sampling site. The lancet sled 40 is stopped in the extended position by a stop member such as an inside wall of the carriage, the housing, an endcap, or another structure. In any case, the lancet sled stop and the carrier stop preferably are two separate structures, that is, they are not one and the same (even though they may both be defined by the endap or the housing or another component of the lancing device).

Because the low-mass sled 40 and lancet 42 slide decoupled from the drive mechanism (i.e., they "float") during that portion of the lancing stroke during which the skin is punctured, the subject senses less impact by the sharp lancet tip 44 against the skin than with known lancing devices. This significantly reduces the sensation of pain relative to that resulting from lancing with other devices. After puncturing the skin at the sampling site, the return spring 46 retracts the lancet sled 40 back through the bore 36 of the carriage 22, withdrawing the sharp lancet tip 44 back into the housing 12 to prevent inadvertent needle sticks or bloodborne contamination.

In alternative embodiments, a penetration-depth adjustment mechanism is provided to allow adjustment of the depth of penetration of the lancet tip into the skin of the sampling site. For example, the penetration-depth adjustment mechanism may be provided by a rotatable endcap on the proximal end of the housing, with the endcap joined to the housing by a threaded connection permitting the endcap to be extended and retracted axially relative to the housing by twisting the endcap. In still other alternative embodiments, the endcap has one or more adjustably positionable internal stop members that limit the distance of travel of a lancet.

FIGS. 5-24 show a lancing device 110 according to a second example embodiment of the invention. The lancing device 110 is similar to the lancing device 10 of the first example embodiment. Structural differences include the device 110 combining the carrier and sled into one component, and the addition of an innovative penetration depth adjustment mechanism, as described below.

Referring to FIGS. 5-10, the lancing device 110 includes a housing 112, a drive mechanism, a lancet 142, a cocking mechanism, a trigger mechanism, and an endcap 172. Generally, the housing 112 has a proximal end, a distal end, and one or more sidewalls. The endcap 172 preferably includes an opening or passage through which a lancing tip extends for puncturing. In the depicted embodiment, the endcap is separate from and attached to the housing. Alternatively, the endcap may be integrally formed with the housing into a single piece without depth adjustment capability, in which case the endcap is essentially an endwall of the housing. As such, the term "endcap" as used herein includes any structure at the proximal end of the housing, whether separate from or integral to the housing.

Figure 6:
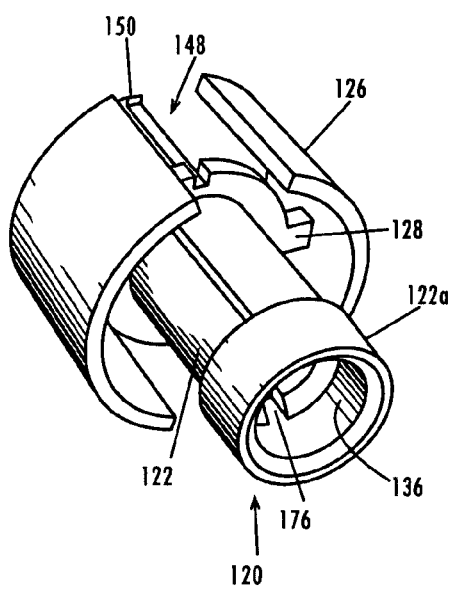
FIG. 6 is a front perspective view of a carrier of the lancing device of FIG. 5.
Figure 7:
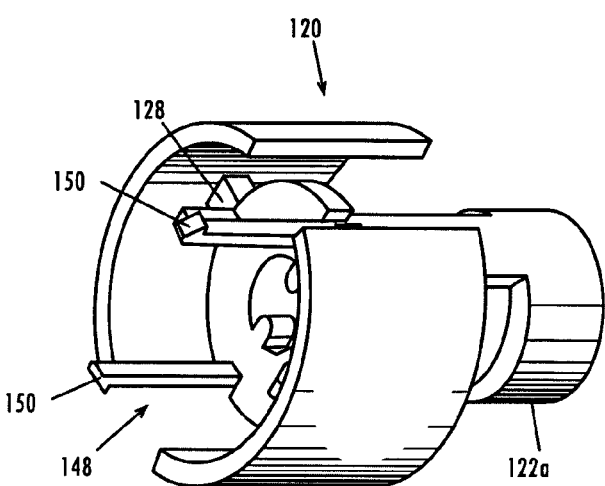
FIG. 7 is a rear perspective view of a carrier of the lancing device of FIG. 5.

The drive mechanism includes a lancet carrier 120, shown with particularity in FIGS. 6 and 7. The lancet carrier 120 preferably includes a carriage 122 mounted within a chamber 124 extending axially through the housing 112, and one or more sleeves or wings 126 extending outwardly of the housing and connected to the carriage by a strut 128 projecting through a slot 130 in the housing. The carriage 122 translations along an axial path parallel to direction arrow "a." A proximal hole or opening is formed at the proximal end of the carriage 122 of the carrier 120 for allowing passage of a lancet tip during lancing, as described below. A bore 136 preferably extends axially through the carriage 122 of the carrier 120. The bore 136 is preferably cylindrical, but it may have a square of other cross-sectional shape, if desired. And the drive mechanism further includes a drive spring 154 that is preferably engaged between the carrier 120 and the housing 112, for driving the carrier and lancet 142 through a lancing stroke from the cocked position (see FIG. 14) to the extended position (see FIG. 19).

The lancet 142 is preferably slidably mounted within the bore 136 of the carriage 122, and includes a lancet body 143 and a sharp lancing tip 144. The bore 136 is preferably cylindrical, but it may have a square of other cross-sectional shape, if desired, and is axially longer than the lancet body 143. Alternatively, the carriage 122 may be provided by a disc, piston, finger, or other drive member that pushes the lancet 142, but that does not have a bore for receiving it, so that the lancet sliding floats relative to the carriage and in the chamber 124. The lancet 42 may be of a conventional type, or it may have special features for cooperating with the endcap to control the penetration depth, as described below. The lancet 142 preferably has a low mass relative to known lancets. A return spring 146 is preferably engaged between the lancet body 143 and the endcap 172.

The cocking mechanism preferably comprises at least one cocking arm and engagement surface for securing the carrier in a cocked position. In the depicted embodiment, for example, the cocking mechanism has two cocking arms 148 that extend distally from the carrier 140, each with a catch such as a barb 150 for engaging an engagement surface such as a flange or shoulder 152 of the housing 112, as shown in FIG. 13.

The trigger mechanism preferably comprises a trigger spring 164 and a release button 160. The release button 160 preferably includes a catch release member such as a cam face 162 for engagement against a cooperating inclined face 163 or other catch release member of the cocking arm 148, as shown in FIG. 16.

In alternative embodiments, the carrier 120 is included in other lancing devices in which the lancet fits snugly therein without slidably floating therein so that the lancet and carrier do not decouple during the lancing stroke. In this way, the carriage of the carrier acts as a conventional lancet holder. Such lancing devices may include the cocking and trigger mechanisms described herein or others. While these lancing devices do not produce the pain-reducing advantages associated with decoupling the lancet from the drive mechanism, they nevertheless provide improved guidance and control of the lancet, which tends to reduce lateral movement and rocking of the lancet and thereby reduce pain sensed during puncturing.

Figure 10:
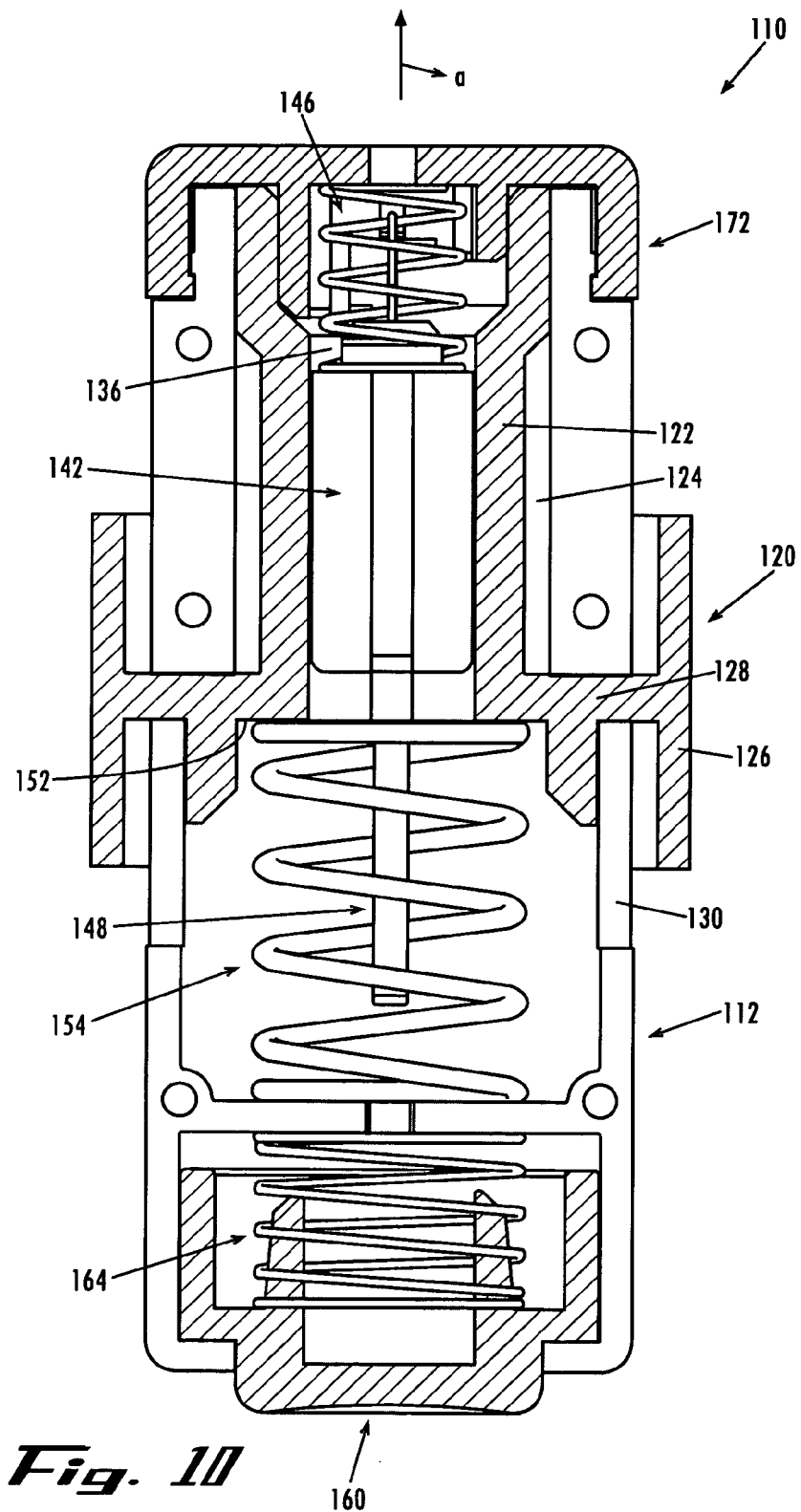
FIG. 10 is a longitudinal cross-section view of the lancing device of FIG. 5, with the lancet and carrier in a rest position.
Figure 11:
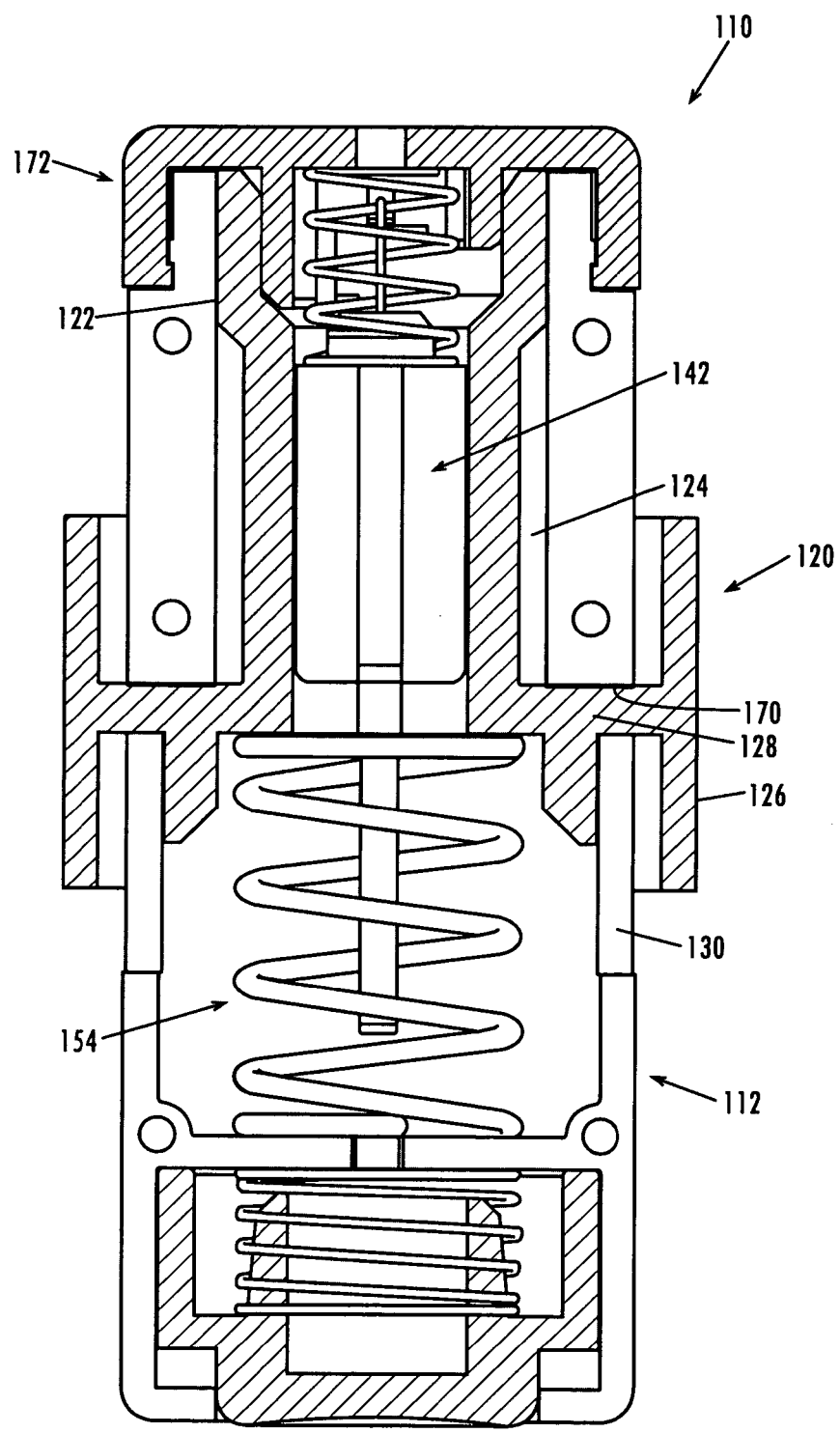
FIG. 11 is a longitudinal cross-section view of the lancing device of FIG. 5, with the lancet and carrier in a retracted position.

FIGS. 10-18 depict a sequence of operation of the lancing device 110 and a second example method of lancing according to the present invention. As shown in FIG. 10, the lancing device 110 is preferably delivered to the user in an uncocked, rest state, with the drive spring 54 substantially or partially relaxed. The user cocks the device 110 by gripping the housing 112 and the wings 126, and pulling the wings (and thereby the carriage 122 and lancet 142) distally relative to the housing, into the cocked position shown in FIGS. 11-13, with the drive spring 154 substantially fully compressed. The return spring 146 withdraws the lancet 142 distally along with the carrier 120 during cocking. Engagement of the cocking arm catch barb 150 with the engagement shoulder 152 retains the carrier 120 in the cocked position after the wings 126 are released, as shown in FIG. 13.

The user then places the proximal face of the housing 112 against the skin at the sampling site of a human or animal subject. The device 110 is fired to complete the lancing operation by pressing the release button 160, as shown in FIGS. 14-16. When this is done, the inclined face 162 of the release button 160 contacts the cooperating inclined face 163 of the cocking arm 148 and disengages the catch barb 150 from the engagement shoulder 152, as shown in FIG. 16. Upon operating the trigger mechanism, the carrier 120 is released and the lancing stroke is initiated. The carrier 120 is now propelled forward under the influence of the drive spring 154, carrying the lancet 142 along with it.

The carrier 120 and lancet 142 move forward together until there is an impact with a carrier stop such as a proximal endwall 170 of the slot 130 in the housing 112. For example, the stopping may be caused by the carrier struts 128 impacting the housing slot proximal endwalls 170 (as shown in FIG. 17), a proximal face of the carriage 122 impacting a distal face of the endcap 172, or by other means. Inertia propels the lancet 142 forward after the carrier 120 stops, with the lancet 142 no longer being coupled to the carrier 120 or the spring 144 of the drive mechanism.

Figure 18:
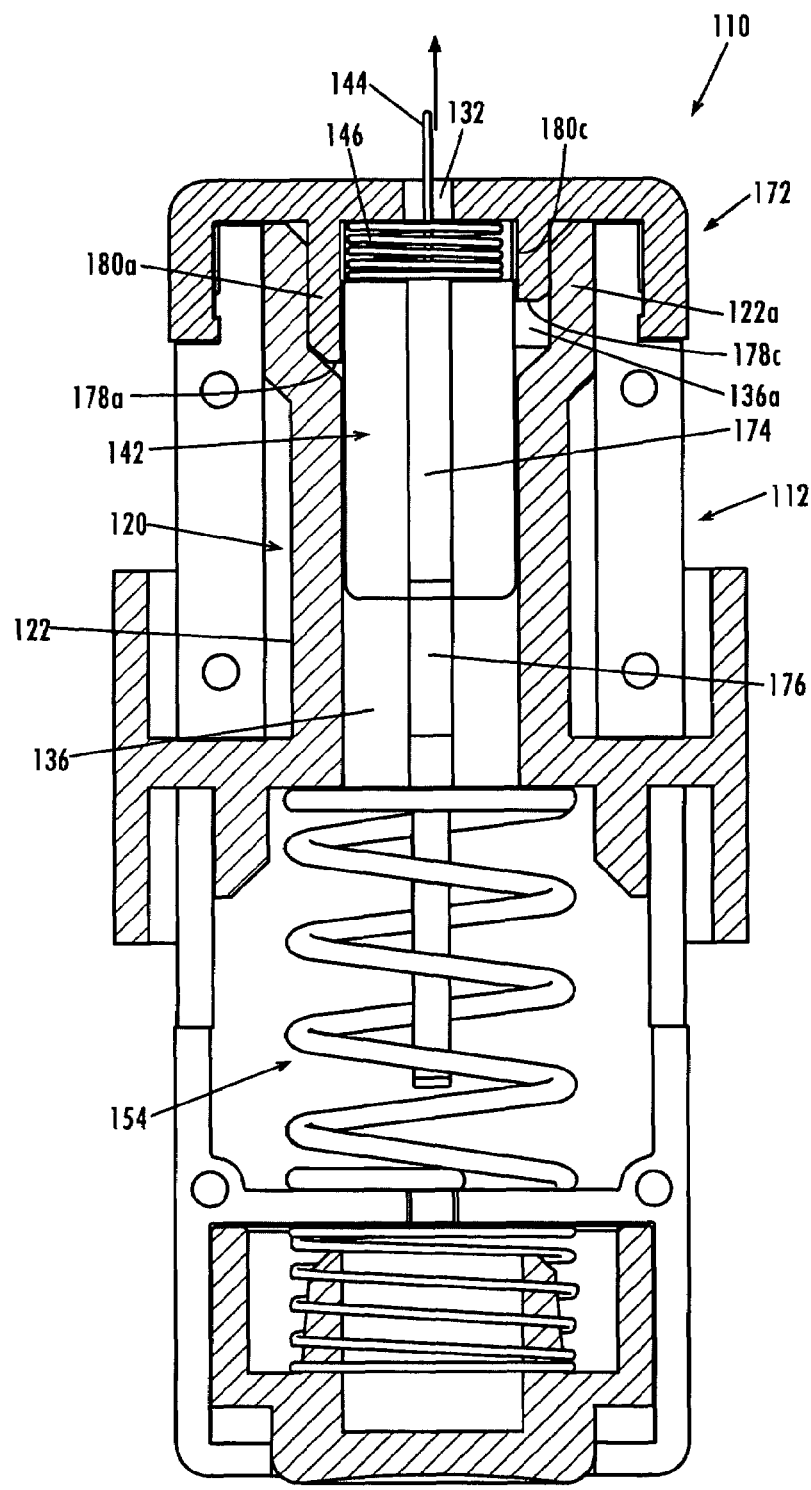
FIG. 18 is a longitudinal cross-section view of the lancing device of FIG. 5, with the carrier stopped and the lancet continuing to the extended or puncturing position.

The lancet 142 slides forward through the bore 136 of the carriage 122 to the extended position, shown in FIG. 18, wherein the sharp lancet tip 144 passes through a hole or opening 132 in the endcap 172 and projects a distance beyond the endcap to puncture the subject's skin at the sampling site. Because the low-mass lancet 142 floats decoupled from the drive mechanism of the device 110 during that portion of the lancing stroke during which the skin is punctured, the subject senses less impact by the sharp lancet tip 144 against the skin than with known lancing devices. This significantly reduces the sensation of pain relative to that resulting from lancing with other devices. After puncturing the skin at the sampling site, the return spring 146 retracts the lancet 142 back through the bore 136 of the carriage 122, withdrawing the sharp lancet tip 144 back into the housing 112 to prevent inadvertent needle sticks or bloodborne contamination.

In addition, a penetration-depth adjustment mechanism may be provided to allow adjustment of the depth of penetration of the lancet tip into the skin of the sampling site. For example, the penetration-depth adjustment mechanism may be provided by a uniquely configured carrier 120, lancet 142, and endcap 172, as shown in FIGS. 6-9 and 19-25. The carrier 120 and the lancet 142 are keyed so that they fit together in a specific orientation. Preferably, the lancet 142 has at least one male key member and the carrier 120 has at least one female key member, or vice-versa, that cooperate to properly orient the lancet. In addition, the lancet 142 has at least one contact surface and the endcap 172 has a plurality of stop surfaces, or vice versa, for adjusting the puncturing depth of the lancet tip.

Figure 8:
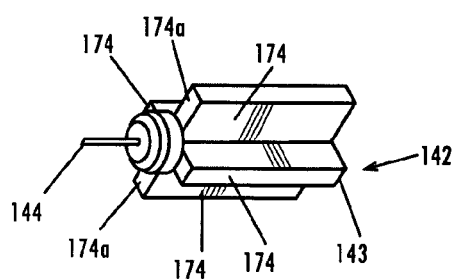
FIG. 8 is a front perspective view of a lancet of the lancing device of FIG. 5.
Figure 9:
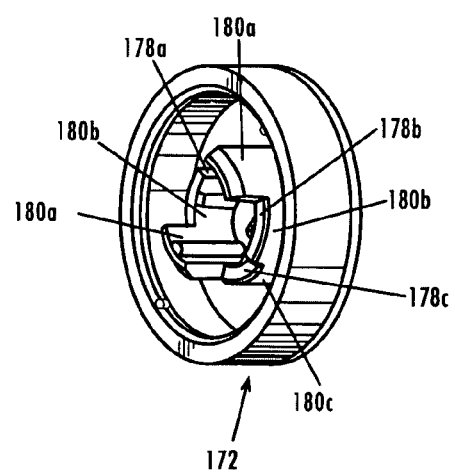
FIG. 9 is a rear perspective view of an endcap of the lancing device of FIG. 5.

In the depicted embodiment, for example, the lancet body 143 comprises four arms 174 in the shape of a "t" with two opposing ones of the arms having outer portions 174a making them longer than the other two arms (see FIGS. 8 and 25). The two male key members and two contact surfaces are formed by the same structure, namely, the two outer portions 174a of the arms 174 of the lancet body 143. The two arm outer portions 174a are received in two female key channels 176 in the carrier 120 to properly orient the lancet 142 (see FIGS. 6, 18, 19, and 25). And to provide penetration depth adjustability, the two arm outer portions 174a selectively engage two sets of three stop surfaces 178a, 178b, and 178c (collectively, the "stop surfaces 178") defined by protrusions 180a, 180b, and 180c (collectively, the "protrusions 180") extending distally from the endcap 172 (see FIGS. 9, 18 and 19). It will be understood that another number of protrusions 180 and stop surfaces 178 may be provided, as may be desired for a given application.

The protrusions 180 are circumferentially arranged relative to the lancet 142, so that the arms 174 without outer portions 174a are circumscribed by the circumferential protrusions, but the outer portions interfere with the protrusions when they are in alignment (see FIG. 25). In this way, the endcap 172 can be rotated so that one of the three protrusions 180 of each protrusion set aligns with and contacts the two outer portions 174a to stop the lancet 142, while the other two protrusions of each set are out of alignment with the outer portions and do not interfere with the lancet. Preferably, the carriage 122 has a flared proximal section 122a with a flared bore 136a that receives the two protrusions 180 that are not aligned with the outer portions 174a of the longer arms 174 (see FIGS. 6, 18, and 25). The flared bore 136a has a larger diameter or other size-indicating dimension than the bore 136.

FIGS. 20-24 show the use of the adjustment mechanism and a method of adjusting a lancing device for various penetration depth settings. In FIG. 20, the endcap 172 is positioned with the first/longest protrusions 180a aligned with the arm outer portions 174a, so that if the lancing device is accidentally fired the lancing tip 144 will not extend beyond the endcap.

In FIG. 21, the endcap 172 has been rotated (in the direction of arrow "r") to a shallow puncturing depth position with the second/intermediate length protrusions 180b aligned with the arm outer portions 174a. In FIG. 22, the lancet 142 has been fired and is in the puncturing position, with the second/intermediate length protrusions 180b contacting the arm outer portions 174a to stop the lancet in the shallow puncturing depth position.

In FIG. 23, the endcap 172 has been rotated farther to a deep puncturing depth position with the third/shortest length protrusions 180c aligned with the arm outer portions 174a. In FIG. 24, the lancet 142 has been fired and is in the puncturing position, with the third/shortest length protrusions 180c contacting the arm outer portions 174a to stop the lancet later, in the deep puncturing depth position.

It will be understood that the adjustment mechanism can be provided in alternative forms. In one alternative embodiment, the carrier 120 and the endcap 172 are the same, but the lancet 242 has a body 243 that generally conforms to the shape of the bore 136 defined in the carriage 122 and that has outer portions 274a extending therefrom (see FIG. 26). In another alternative embodiment, the endcap protrusions that are not aligned with the outer portions are received in recesses in the lancet body to avoid movement-limiting interference with the lancet. And in another alternative embodiment, the adjustment mechanism is included in lancing device with a lancet that is coupled to the drive mechanism so that it does not float separately therefrom, with the female key channels or other structures being defined in the housing or another component of the lancing device.

Accordingly, it can be seen that the present invention provides advantages over other lancing devices. In particular, the present invention includes lancing devices in which the drive mechanism is decoupled from lancet so that, when the skin is pierced, the lancet floats free of the mass of the drive mechanism. Because of this decoupling and free-floating, there is less mass behind the lancet tip when impacting the skin, which reduces the pain felt by the user. In addition, because the drive spring is decoupled from the lancet when the skin is pierced, this prevents restrikes from spring-induced lancet oscillations. Furthermore, the lancet has a high velocity relative to previous lancing devices because of the reduced mass/energy ratio from decoupling the lancet from the drive mechanism.

It should be understood that the foregoing relates only to example embodiments of the present invention, and that numerous changes, additions, modifications and deletions may be made from the example embodiments described without departing from the spirit and scope of the invention as defined by the following claims.

What is claimed is:

1. A lancing device comprising:
    a drive mechanism comprising a drive spring and a carrier driven by the drive spring; and
    a lancet that is decoupled from the drive mechanism and slidably floats relative to the carrier during at least a portion of a lancing stroke,
    further comprising a housing defining an axial chamber, wherein the carrier comprises:
        a carriage slidably received in the housing chamber, the carriage defining a bore that slidably receives the lancet; and
        one or more wings extending outwardly of the housing, wherein the lancing device is armed by retracting the wings to a cocked position with the carrier in a retracted position,
        further comprising one or more struts extending between the carriage and the wings, and projecting through one or more slots in the housing, wherein, after the lancing device is fired but before the lancet reaches an extended position, the carrier is stopped by the carrier struts engaging one or more stop surfaces defined by the housing slots.

2. The lancing device of claim 1, wherein the carrier engages and drives the lancet through a first portion of the lancing stroke, and wherein the lancet is inertially propelled through a second portion of the lancing stroke after the carrier is stopped.

3. The lancing device of claim 1, wherein the lancing stroke includes the lancet moving from a retracted position to an extended position, wherein the drive mechanism is decoupled from the lancet when the lancet is in the extended position.

4. The lancing device of claim 3, further comprising a carrier stop member that limits the travel of the carrier before the lancet reaches the extended position.

5. The lancing device of claim 4, wherein the carrier stop does not limit the travel of the lancet, wherein, after the carrier is stopped by the carrier stop, the lancet decouples from the carrier and slidably floats relative to the carrier as it continues moving toward the extended position.

6. The lancing device of claim 4, further comprising a lancet stop member that limits the travel of the lancet in the extended position, the lancet stop being a separate structure from the carrier stop.

7. The lancing device of claim 1, further comprising a sled that receives or includes the lancet and that is slidably received in the carrier.

8. The lancing device of claim 7, further comprising a cocking mechanism comprising at least one cocking arm extending from the drive mechanism and an engagement surface for retaining the cocking arm in a cocked position with the carrier in a retracted position, wherein the cocking arm extends from the sled.

9. The lancing device of claim 1, further comprising a cocking mechanism comprising at least one cocking arm extending from the drive mechanism, and an engagement surface for retaining the cocking arm in a cocked position with the carrier in a retracted position.

10. The lancing device of claim 9, further comprising a trigger mechanism including a release button with a catch release member that, when the release button is moved, engages the cocking arm and releases the carrier to move to an extended position.

11. The lancing device of claim 9, wherein the cocking arm extends from the carrier.

12. The lancing device of claim 1, further comprising an endcap with at least a portion that rotates to adjust a penetration depth of the lancet.

13. A lancing device comprising:
a housing defining an axial chamber;
a lancet moveable through a lancing stroke between a retracted position and an extended position; and
a drive mechanism including a drive spring and a carrier, wherein the carrier comprising a carriage slidably received in the housing chamber, the carriage defining a bore that slidably receives the lancet, one or more wings extending outwardly of the housing, and one or more struts extending between the carriage and the wings and projecting through one or more slots in the housing,
wherein the lancing device is armed by retracting the wings to a cocked position with the carrier in the retracted position and, after the lancing device is fired, the carrier is driven by the drive spring and in response thereto engages and drives the lancet through a first portion of the lancing stroke until the carrier is stopped by the carrier struts engaging one or more stop surface defined by the housing slots, and the lancet is decoupled from the carrier and inertially propelled through a second portion of the lancing stroke after the carrier is stopped.

14. The lancing device of claim 13, further comprising a cocking mechanism including at least one cocking arm extending from the drive mechanism and defining a catch surface, and an engagement surface defined by the housing for retaining the catch surface with the carrier in the retracted position, and further comprising a trigger mechanism including a release button with a catch release member that, when the release button is moved, engages the catch surface of the cocking arm and releases the carrier to move to the extended position.

15. A lancing device comprising:
a housing;
a lancet defining at least one contact surface;
a drive mechanism including a drive member that engages and drives the lancet; and
an endcap that rotates relative to the housing and that has a plurality of stop surface that are selectively aligned with and engaged by the lancet contact surface to limit forward lancet movement,
wherein the drive member comprises a carriage that receives the lancet and that has a flared proximal section defining a flared bore that receives the endcap stop surfaces not aligned with and engaged by the lancet body engagement surface.

16. The lancing device of claim 15, wherein the drive mechanism and the lancet each have at least one key member and the key members cooperate to orient the lancet within the housing.

17. The lancing device of claim 16, wherein the lancet body is T-shaped with four arms defining the at least one lancet key member, wherein at least one of the arms is longer than the other arms.

18. The lancing device of claim 15, wherein the lancet body includes at least one radially extending arm defining at least one lancet key member and also defining the at least one lancet contact surface.

19. The lancing device of claim 15, wherein the endcap stop surfaces are defined by protrusions extending distally from the endcap.

20. The lancing device of claim 19, wherein the protrusions are arranged generally circumferentially relative to the lancet so that the lancet contact surface interferes with the protrusions to stop the lancet but the rest of the lancet is circumscribed by the protrusions.

* * * * *